US012203951B2

(12) United States Patent
Yamada

(10) Patent No.: US 12,203,951 B2
(45) Date of Patent: Jan. 21, 2025

(54) AUTOMATED ANALYSIS DEVICE, AND ANALYSIS METHOD

(71) Applicant: Hitachi High-Tech Corporation, Tokyo (JP)

(72) Inventor: Takumi Yamada, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 923 days.

(21) Appl. No.: 17/294,029

(22) PCT Filed: Nov. 22, 2019

(86) PCT No.: PCT/JP2019/045764
§ 371 (c)(1),
(2) Date: May 14, 2021

(87) PCT Pub. No.: WO2020/129537
PCT Pub. Date: Jun. 25, 2020

(65) Prior Publication Data
US 2022/0011330 A1   Jan. 13, 2022

(30) Foreign Application Priority Data
Dec. 19, 2018   (JP) ................. 2018-237068

(51) Int. Cl.
*B01L 3/00*      (2006.01)
*A61L 27/16*    (2006.01)
(Continued)

(52) U.S. Cl.
CPC ... *G01N 35/00732* (2013.01); *G01N 35/0095* (2013.01); *G01N 2035/00831* (2013.01)

(58) Field of Classification Search
CPC ......... G01N 35/00732; G01N 35/0095; G01N 2035/00831; G01N 2035/0446; G01N 35/0092; G16H 10/40
See application file for complete search history.

(56) References Cited

U.S. PATENT DOCUMENTS

2019/0041386 A1    2/2019  Yabutani et al.

FOREIGN PATENT DOCUMENTS

JP        2016-156628 A      9/2016
WO    WO-2017159359 A1 *  9/2017   ......... G01N 33/5304

OTHER PUBLICATIONS

English Machine Translation of WO2017159359A1, obtained from Google Patents on May 1, 2024, pp. 1-13. (Year: 2024).*

(Continued)

*Primary Examiner* — Jennifer Wecker
*Assistant Examiner* — Oyeleye Alexander Alabi
(74) *Attorney, Agent, or Firm* — Crowell & Moring LLP

(57) ABSTRACT

Since the measurement start timings for a plurality of specimens in different test fields deviate from one another, the measurement results are not coordinated, leading to a delay in reporting. When determining an order for measuring a newly recognized specimen using an automated analysis device capable of performing measurements in a plurality of test fields, the measurement order for specimens waiting to be measured is changed to minimize the time difference between measurement result output timings for a plurality of specimens for the same patient, with reference to specimen information such as urgent test information, a measurement completion time, and an earliest measurement completion time for other specimens, relating to the patient's other specimens having the same patient number in the specimen information.

8 Claims, 12 Drawing Sheets

(51) Int. Cl.

| | |
|---|---|
| *A61L 27/56* | (2006.01) |
| *B01F 23/00* | (2022.01) |
| *B01F 23/41* | (2022.01) |
| *B01F 101/23* | (2022.01) |
| *B01L 7/00* | (2006.01) |
| *B01L 9/00* | (2006.01) |
| *B23Q 17/24* | (2006.01) |
| *C07K 14/705* | (2006.01) |
| *C08F 220/56* | (2006.01) |
| *C08L 33/26* | (2006.01) |
| *C12M 1/34* | (2006.01) |
| *C12Q 1/04* | (2006.01) |
| *C12Q 1/18* | (2006.01) |
| *C12Q 1/6844* | (2018.01) |
| *C12Q 1/686* | (2018.01) |
| *G01N 1/31* | (2006.01) |
| *G01N 15/00* | (2024.01) |
| *G01N 15/02* | (2024.01) |
| *G01N 21/17* | (2006.01) |
| *G01N 21/3577* | (2014.01) |
| *G01N 21/359* | (2014.01) |
| *G01N 21/39* | (2006.01) |
| *G01N 21/45* | (2006.01) |
| *G01N 21/64* | (2006.01) |
| *G01N 21/77* | (2006.01) |
| *G01N 21/78* | (2006.01) |
| *G01N 27/10* | (2006.01) |
| *G01N 27/414* | (2006.01) |
| *G01N 30/12* | (2006.01) |
| *G01N 30/68* | (2006.01) |
| *G01N 30/70* | (2006.01) |
| *G01N 30/72* | (2006.01) |
| *G01N 30/88* | (2006.01) |
| *G01N 33/00* | (2006.01) |
| *G01N 33/18* | (2006.01) |
| *G01N 33/50* | (2006.01) |
| *G01N 33/53* | (2006.01) |
| *G01N 33/543* | (2006.01) |
| *G01N 33/68* | (2006.01) |
| *G01N 33/74* | (2006.01) |
| *G01N 35/00* | (2006.01) |
| *G01N 35/10* | (2006.01) |
| *G06T 7/00* | (2017.01) |
| *G06T 7/90* | (2017.01) |
| *H10K 10/46* | (2023.01) |
| *H10K 85/00* | (2023.01) |
| *H10K 85/20* | (2023.01) |

(56) References Cited

OTHER PUBLICATIONS

International Search Report (PCT/ISA/210) issued in PCT Application No. PCT/JP2019/045764 dated Jan. 21, 2020 with English translation (four (4) pages).

Japanese-language Written Opinion (PCT/ISA/237) issued in PCT Application No. PCT/JP2019/045764 dated Jan. 21, 2020 (five (5) pages).

* cited by examiner

[FIG. 1]
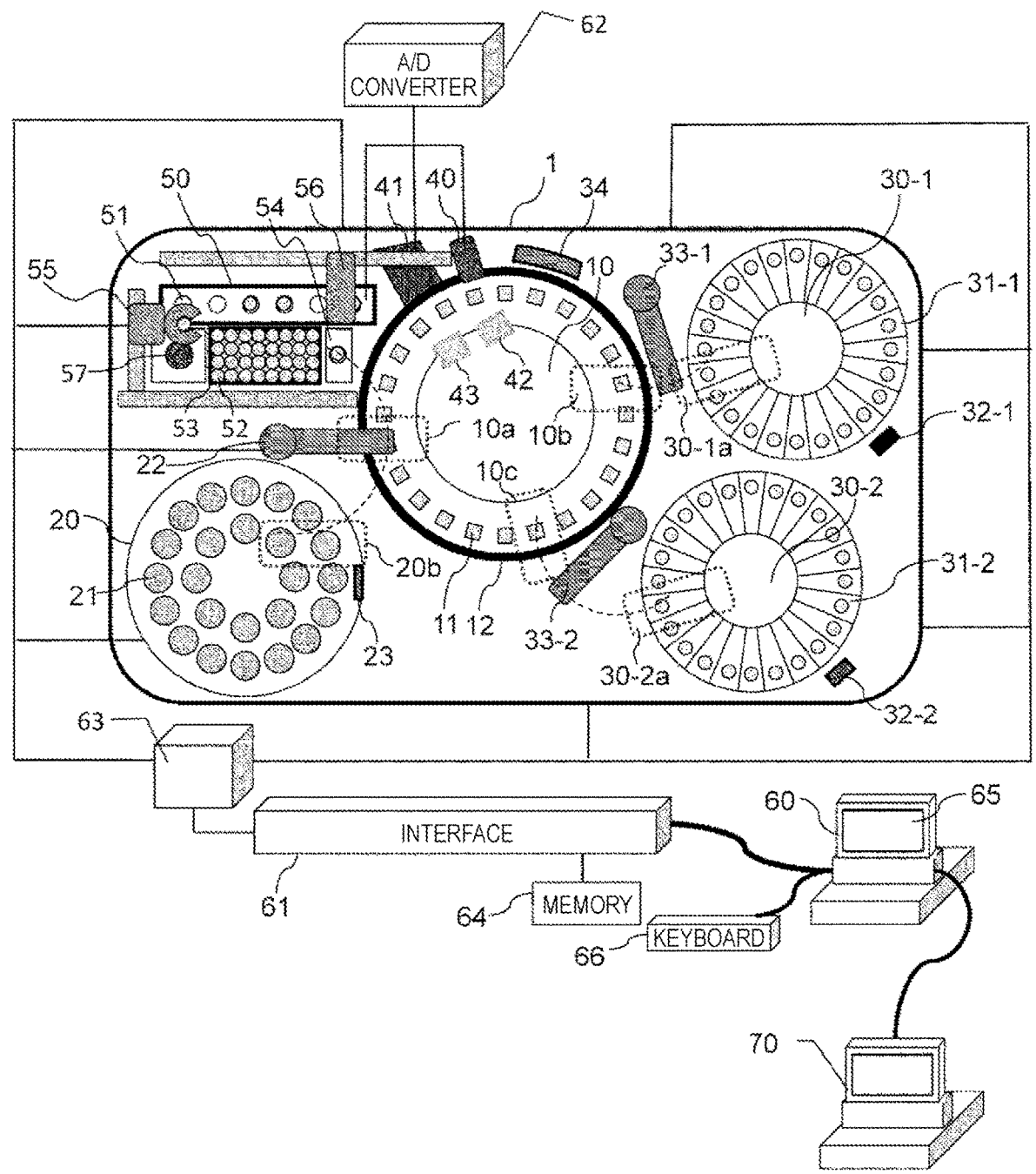

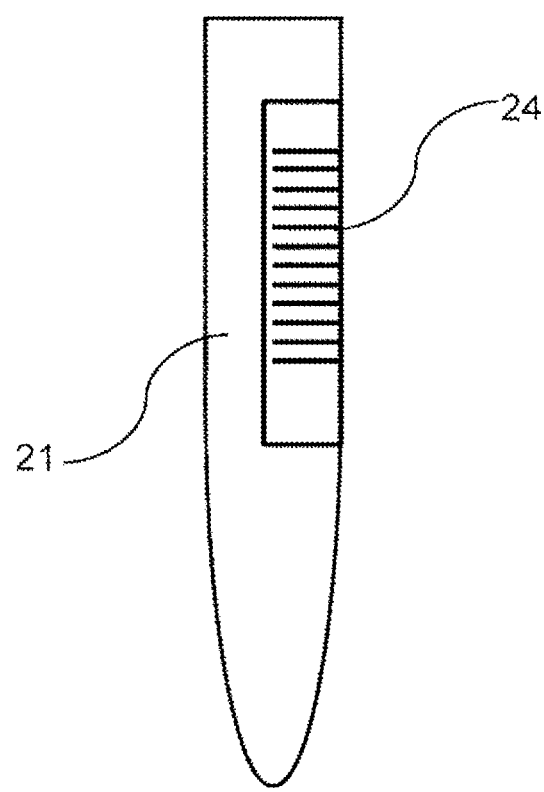
[FIG. 2]

[FIG. 3]
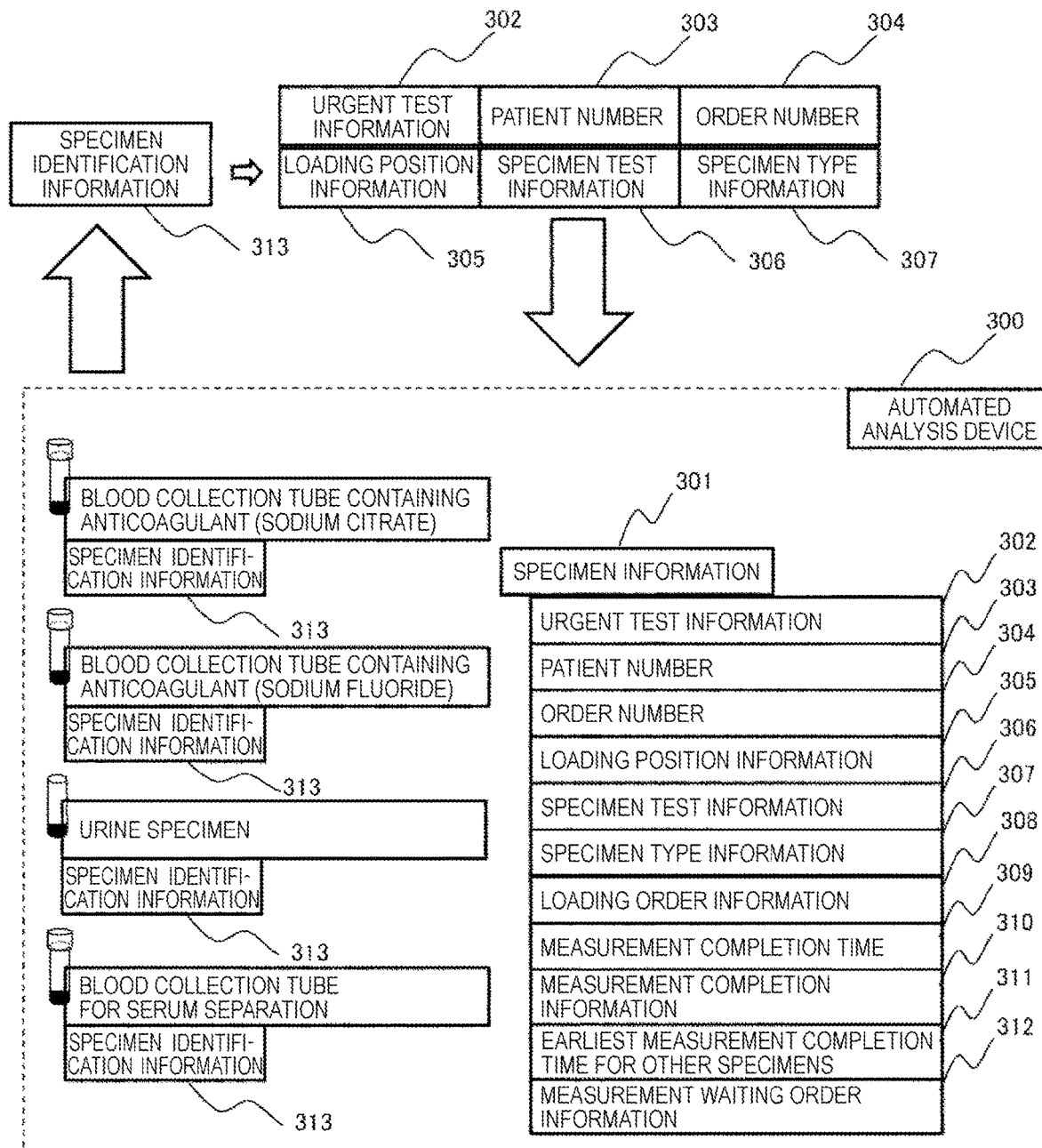

[FIG. 4]
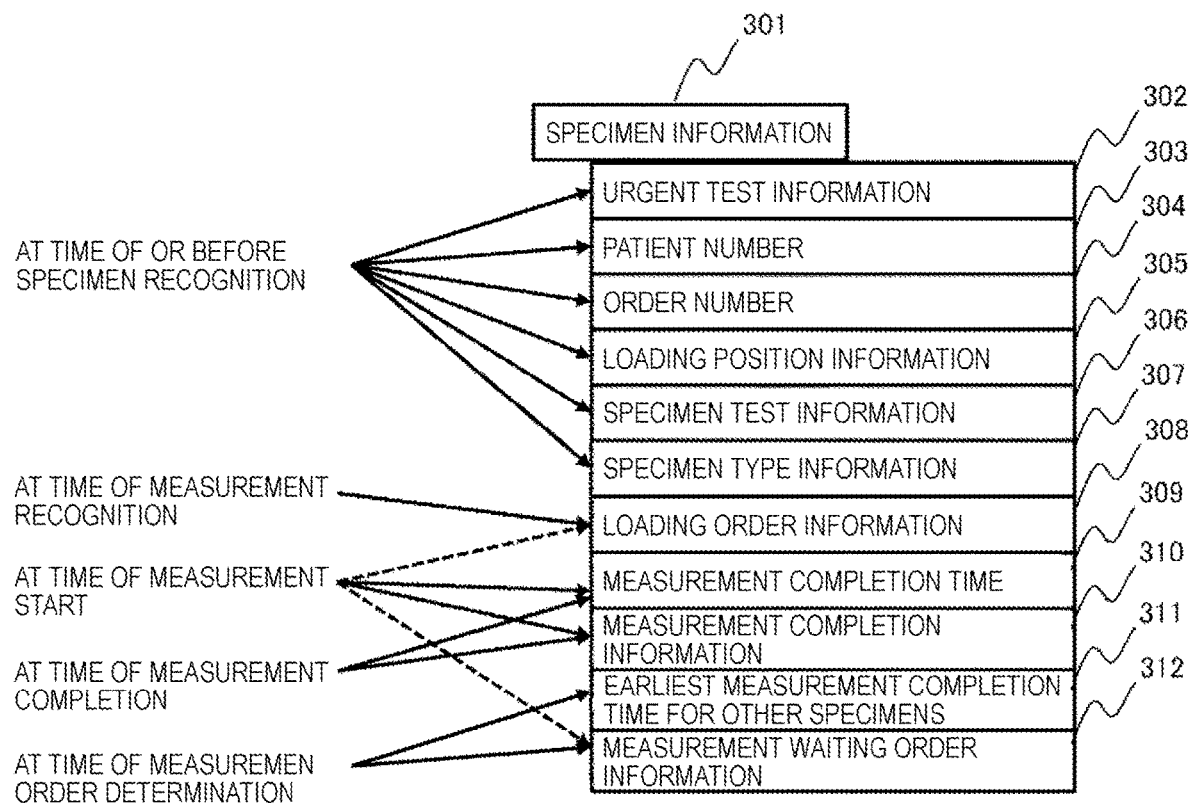

[FIG. 5]
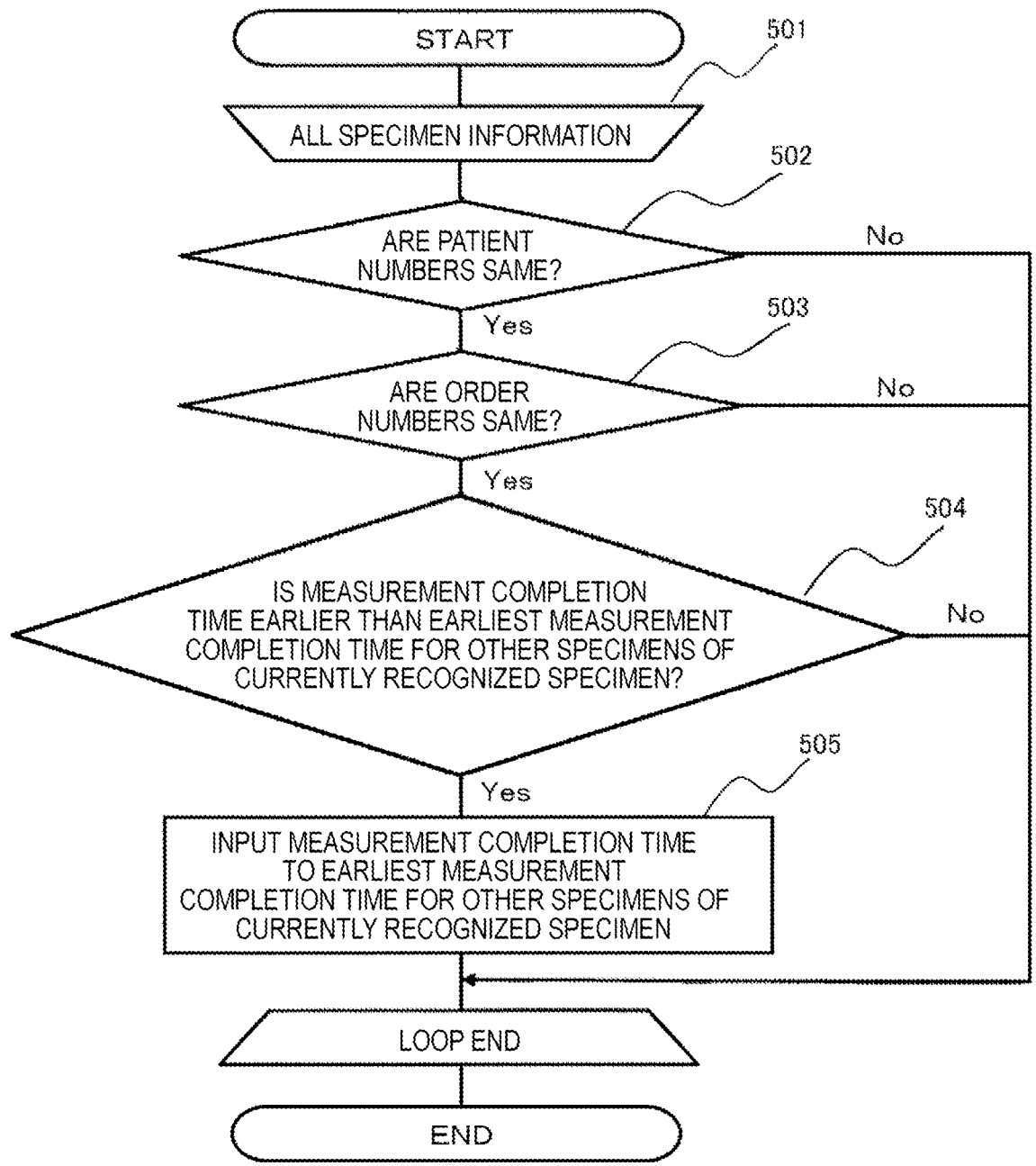

[FIG. 6]
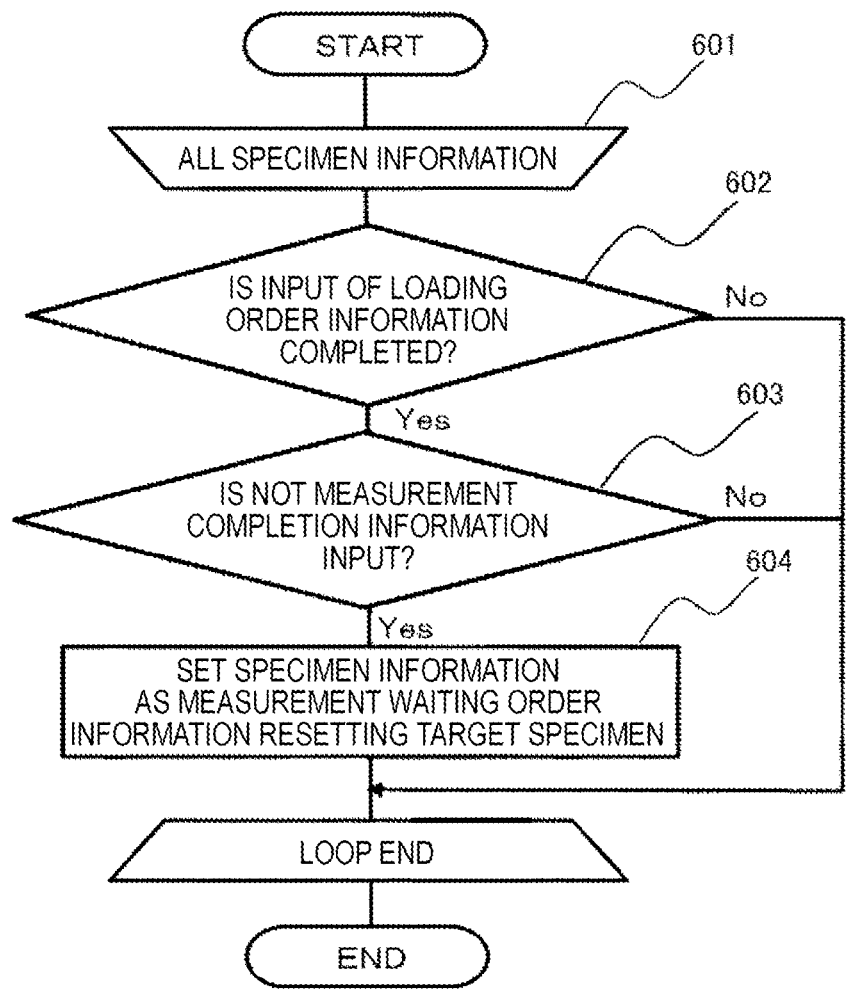

[FIG. 7]
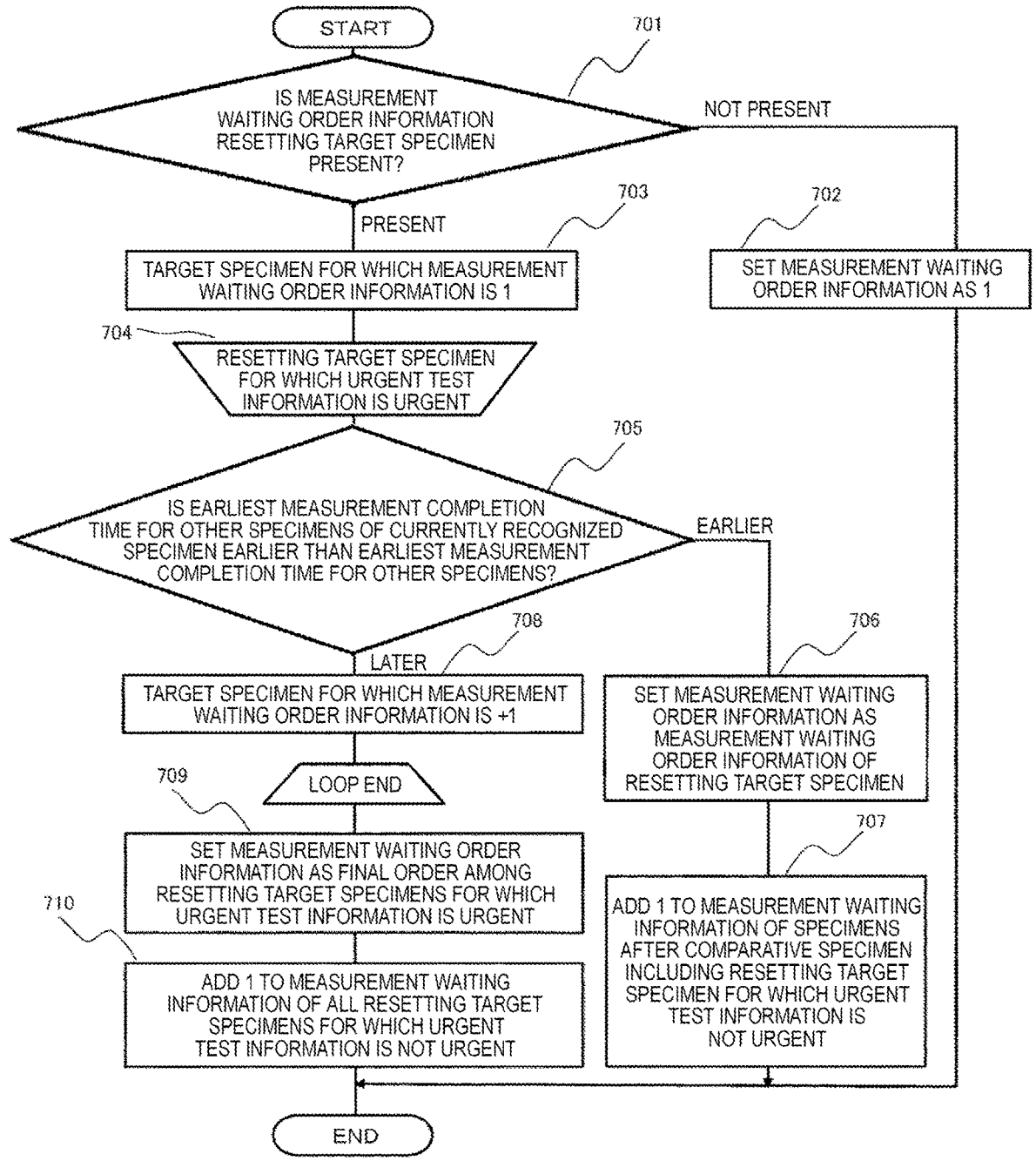

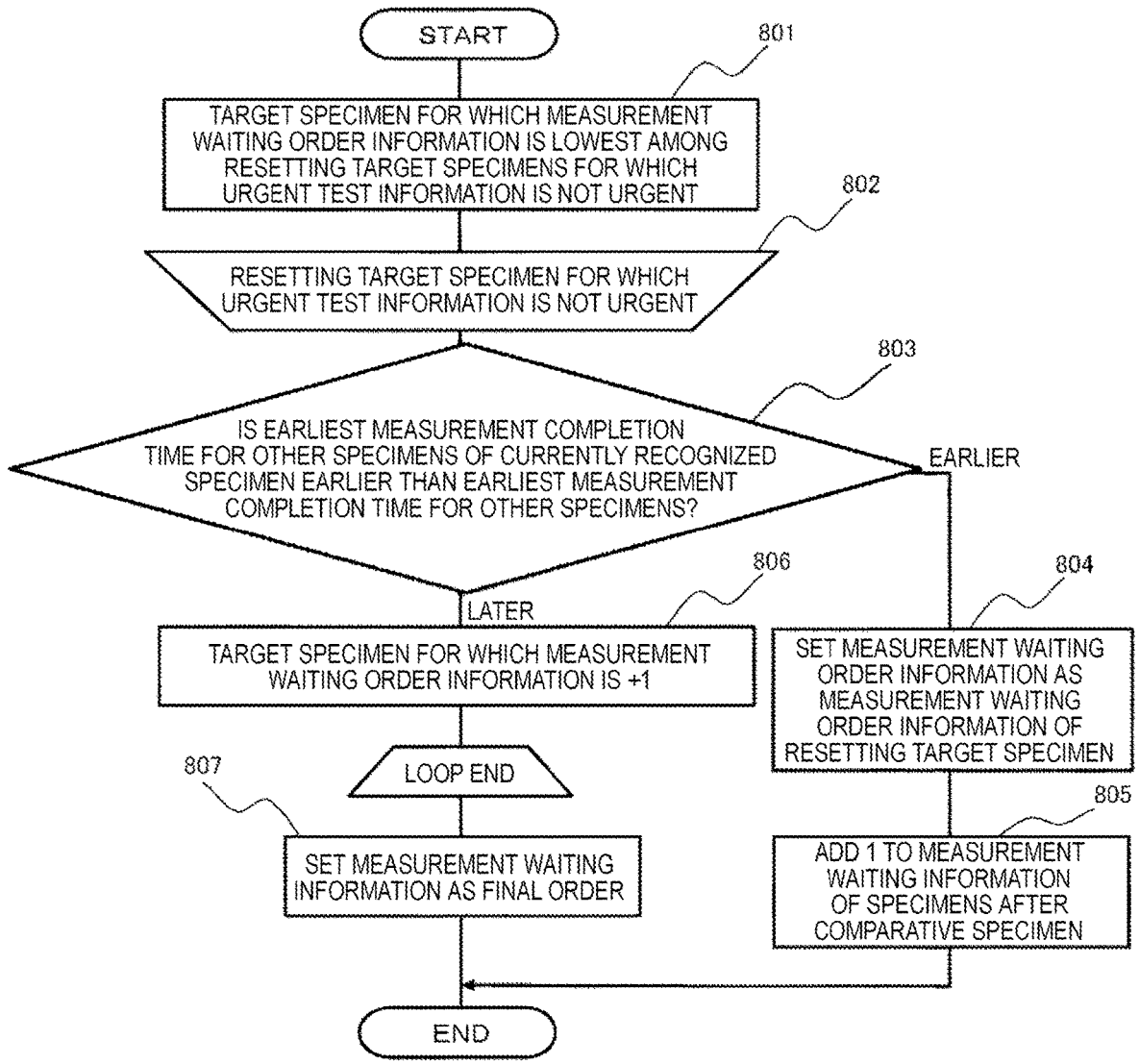

[FIG. 9]

MEASUREMENT ORDER MONITOR

— 900

— 901

| MEASURE-MENT ORDER | URGENT | SPECIMEN ID | PATIENT NUMBER | ORDER NUMBER | POSITION | SPECIMEN TYPE | EARLIEST MEASUREMENT COMPLETION TIME FOR OTHER SPECIMENS |
|---|---|---|---|---|---|---|---|
| 1 | E | 09130001001 | 000001 | 0001 | 101 | SERUM | |
| 2 | E | 09130002003 | 000010 | 0002 | 102 | HbA1c | |
| 3 | | 09130101001 | 000101 | 0003 | 1 | SERUM | 07:00 |
| 4 | | 09130112001 | 000025 | 0004 | 2 | SERUM | 07:15 |
| 5 | | 09130101002 | 000030 | 0005 | 11 | COAGULATION | |
| 6 | | 09130102002 | 000015 | 0003 | 12 | COAGULATION | |

SAME PATIENT SPECIMEN MONITOR — 903

CLOSE

SAME PATIENT SPECIMEN MONITOR

PATIENT NUMBER: 000101
ORDER NUMBER: 0003

| SPECIMEN TYPE | POSITION | MEASUREMENT COMPLETION TIME | EARLIEST MEASUREMENT COMPLETION TIME FOR OTHER SPECIMENS |
|---|---|---|---|
| HbA1c | 51 | 07:00 | |
| COAGULATION | 71 | 07:20 | 07:00 |
| SERUM | 1 | | 07:00 |

SAMPLE DISK POSITION MONITOR | MEASUREMENT RESULT | CLOSE

[FIG. 11]
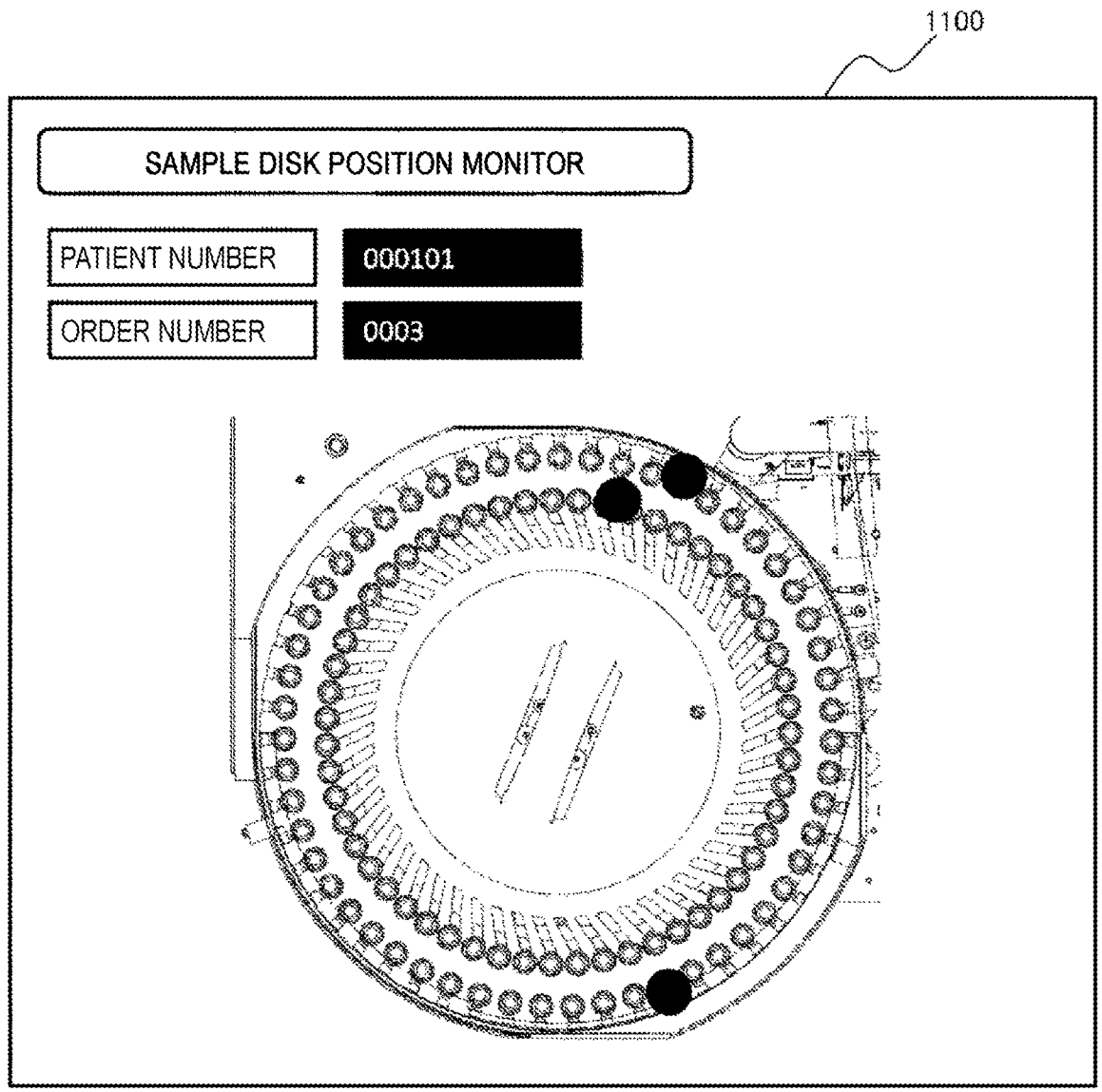

[FIG. 12]
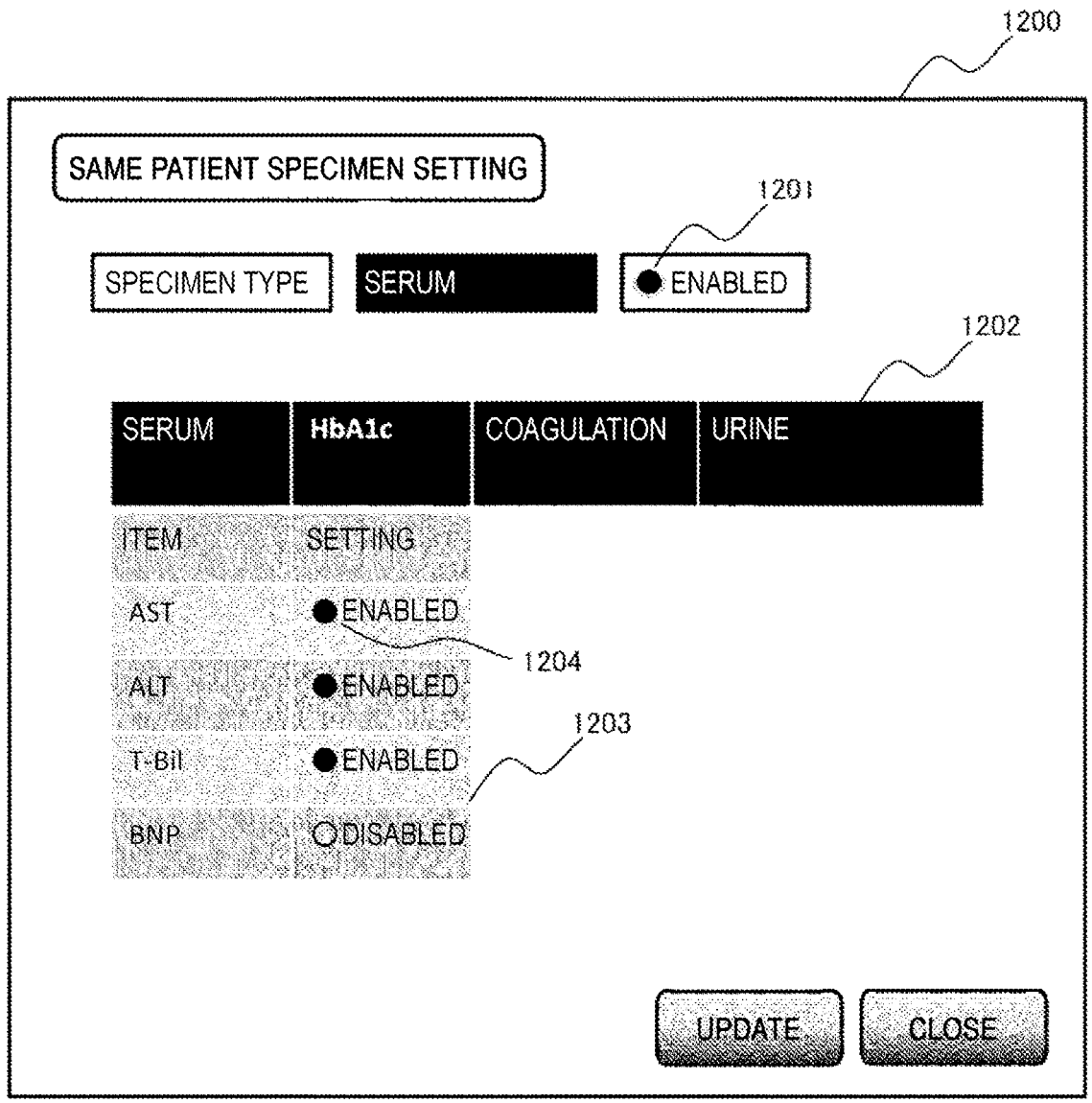

AUTOMATED ANALYSIS DEVICE, AND ANALYSIS METHOD

TECHNICAL FIELD

The present invention relates to an automated analysis device that analyzes the amount of a component in a specimen and particularly relates to an automated analysis technique capable of analyzing items in different test fields at the same time.

BACKGROUND ART

Specimen tests in which specimens such as blood or urine are handled are classified into a plurality of test fields such as a biochemical test, an immunological test, a blood coagulation test, or a complete blood count test, and a plurality of test results are comprehensively considered and used for diagnosis or for checking a treatment effect. In order to obtain a plurality of test results, specimens of the same patient need to be collected into different blood collection tubes such as a blood collection tube for serum separation, a blood collection tube containing an anticoagulant (sodium citrate), a blood collection tube containing an anticoagulant (sodium fluoride), or a blood collection tube containing an anticoagulant (EDTA) at the same timing.

In the related art, measurement is executed on these different blood collection tubes in different automated analysis devices. However, recently, measurement can be executed on the different blood collection tubes using a single complex automated analysis device including a plurality of analysis units for executing analysis of different test fields. In a case where a plurality of different specimens obtained from the same patient are measured using the complex automated analysis device and measurement is stagnant in one analysis unit, even when measurement is completed in other analysis units, the results are not coordinated in units of patients, and the measurement results cannot be reported to clinical sites.

PTL 1 relating to this technique discloses a technique in which, in a case where a plurality of specimens having identification information that indicates the same patient further have the same identification information relating to a test, an analysis schedule is determined such that a timing at which measurement for one specimen is to be executed is determined based on a timing at which measurement for another specimen is to be executed or a timing at which the measurement is to be completed.

CITATION LIST

Patent Literature

PTL 1: WO2017/159359

SUMMARY OF INVENTION

Technical Problem

Among specimens that are collected from the same patient and are accommodated indifferent blood collection tubes, some specimens require a pre-treatment such as centrifugal separation depending on the type of analysis. Therefore, in the automated analysis device that executes analysis of different test fields, a specimen that can be loaded on the automated analysis device immediately after being collected, a specimen that requires a pre-treatment such as centrifugal separation but can start to be analyzed within a relatively short period of time, or a specimen that requires a pre-treatment for a long period of time may be an analysis target.

As a result, specimens that are obtained from the same patient but are accommodated in different blood collection tubes corresponding to test fields may be largely different from each other in the time at which the specimen can be loaded in the automated analysis device. For example, regarding specimens of a patient for which a biochemical test and a blood coagulation test are requested, there may also be a case where, when measurement of the biochemical test is about to start, measurement of the blood coagulation test on another specimen of the same patient is already completed. Under this situation, even when the specimens include a specimen for which an urgent test is requested, there was a case that the reporting of the measurement result may be delayed.

PTL 1 describes that, when specimens of the same patient accommodated in different blood collection tubes are continuously analyzed, a timing for the measurement of the biochemical test is determined based on whether or not the measurement of the blood coagulation test is completed. However, the situation where the measurement start time largely varies depending on the difference in the time required for the pre-treatment is not sufficiently handled.

Further, regarding also the same type of test for the same patient, when the test needs to be executed multiple times at predetermined time intervals for one day, for example, when a glycemic load test as a test required for diagnosis of diabetes is executed, it is necessary to make a comprehensive determination using a plurality of measurement results from the standpoint of clinical sites. However, PTL 1 does not consider the reporting of the result about such determination. Therefore, a user needs to manually organize results that are separately output from the device.

An object of the present invention is to solve the above-described problems and to provide an automated analysis device and an analysis method capable of minimizing a time difference between timings at which a plurality of specimen measurement results of the same patient are output even in a situation where there is a large difference in measurement start time.

Solution to Problem

In order to achieve the object, according to the present invention, there is provided an automated analysis device that tests a plurality of test fields, the device including: a specimen container holder portion that holds a specimen container accommodating a specimen; a reagent container holder portion that holds a reagent container accommodating a reagent; a dispensing mechanism that dispenses the specimen and the reagent; a reaction cell holder portion that holds a plurality of reaction cells accommodating a mixed solution of the specimen and the reagent; a first measurement portion that detects light with which the mixed solution is irradiated; a second measurement portion that includes a plurality of measurement channels each of which holds a reaction container accommodating the mixed solution and that detects light with which the reaction container held by each of the measurement channels is irradiated; and a controller that controls a test of the specimen based on specimen identification information read from the specimen container, in which the controller stores specimen information including a patient number read from the specimen identification information and a measurement completion time of the test of the specimen, and determines a measurement order for specimens waiting to be measured based on the stored patient number and the stored measurement completion time.

In order to achieve the object, according to the present invention, there is provided an analysis method for testing a plurality of test fields using an automated analysis device including a first measurement portion that detects light with which a mixed solution of a specimen and a reagent is irradiated, a second measurement portion that includes a plurality of measurement channels each of which holds a reaction container accommodating the mixed solution and that detects light with which the reaction container held by each of the measurement channels is irradiated, and a controller that controls a test of the specimen based on specimen identification information read from the specimen container accommodating the specimen, the analysis method including: allowing the controller to determine a measurement order for specimens waiting to be measured based on specimen information including a patient number read from the specimen identification information and a measurement completion time of the test of the specimen such that a time difference between measurement result output timings for a plurality of specimens for the same patient is minimized.

Advantageous Effects of Invention

According to the present invention, even in a situation where the measurement start time itself largely varies, delayed reporting to clinical sites can be minimized. Objects, configurations, and effects other than those described above will be clarified by describing the following embodiments.

BRIEF DESCRIPTION OF DRAWINGS

FIG. 1 is a diagram illustrating a basic configuration of an automated analysis device according to Embodiment 1.

FIG. 2 is a diagram illustrating an example of a specimen container in Embodiment 1.

FIG. 3 is a diagram illustrating specimen identification information and the like that are handled by the automated analysis device in Embodiment 1.

FIG. 4 is a diagram illustrating a timing at which information is input to specimen information for each specimen in Embodiment 1.

FIG. 5 is a flowchart for inputting an earliest measurement completion time for other specimens of a currently recognized specimen in Embodiment 1.

FIG. 6 is a flowchart for extracting a measurement waiting order information resetting target specimen in Embodiment 1.

FIG. 7 is a flowchart illustrating a measurement waiting order information resetting process when urgent test information of the currently recognized specimen is urgent in Embodiment 1.

FIG. 8 is a flowchart illustrating the measurement waiting order information resetting process when urgent test information of the currently recognized specimen is not urgent in Embodiment 1.

FIG. 9 is a diagram illustrating a measurement order monitor screen example in Embodiment 1.

FIG. 10 is a diagram illustrating a same patient specimen monitor screen example in Embodiment 1.

FIG. 11 is a diagram illustrating a sample disk position monitor screen example in Embodiment 1.

FIG. 12 is a diagram illustrating a same patient specimen setting screen example in Embodiment 1.

DESCRIPTION OF EMBODIMENTS

Hereinafter, an embodiment for embodying the present invention will be sequentially described with reference to the drawings. In this specification, unless specified otherwise, a measurement completion time includes a measurement completion estimated time.

Embodiment 1

Embodiment 1 relates to an automated analysis device and an analysis method in which, when a measurement order for a newly recognized specimen is determined, a measurement order for specimens waiting to be measured is changed with reference to measurement completion times of other specimens for the same patient such that a time difference between specimen measurement result output timings for a plurality of specimens for the same patient can be minimized.

FIG. 1 is a diagram illustrating a basic configuration of a complex automated analysis device according to the present embodiment. As illustrated in FIG. 1, the automated analysis device 1 is mainly configured with a reaction disk 10, a sample disk 20 for specimens, a first reagent disk 30-1, a second reagent disk 30-2, an absorptiometer 40, a light scattering photometer 41, a blood coagulation time measuring unit 50, a computer 60 that causes a display portion to display an operation screen 65, and the like.

The reaction disk 10 that is a reaction container holder portion is a disk-shaped unit that can rotate intermittently in a left-right direction, and a plurality of reaction cells 11 formed of a translucent material can be arranged in a circumferential direction on the reaction disk 10. The reaction cell 11 is held at a predetermined temperature such as 37° C. by a thermostat 12.

On the sample disk 20 that is the specimen container holder portion, a plurality of specimen containers 21 each of which accommodates a biological sample such as blood or urine can be arranged on two inner and outer circles along circumferential direction, respectively, in the example of the configuration illustrated in the drawing. In the vicinity of the sample disk 20, a sample dispensing mechanism 22 is arranged. The sample dispensing mechanism 22 aspirates a predetermined amount of sample from the specimen container 21 positioned at a dispensing (aspiration) position 20b on the sample disk 20 and discharges the samples into the reaction cell 11 positioned at a dispensing (discharge) position 10a on the reaction disk 10.

In the first reagent disk 30-1 and the second reagent disk 30-2 that are the reagent container holder portions, a plurality of first reagent bottles 31-1 and a plurality of second reagent bottles 31-2 to which labels displaying reagent identification information are attached are arranged in circumferential directions of the first reagent disk 30-1 and the second reagent disk 30-2. As the reagent identification information, for example, a barcode or an RFID is used. Here, for example, a case where a barcode is used will be described. Each of the first reagent bottles 31-1 and the second reagent bottles 31-2 accommodates a reagent solution corresponding to an analysis item to be analyzed by the automated analysis device 1.

A first reagent barcode reading device 32-1 and a second reagent barcode reading device 32-2 read reagent barcodes attached to outer walls of the first reagent bottles 31-1 and the second reagent bottles 31-2 during reagent registration. The read reagent information is registered in a memory 64 together with information regarding positions on the first reagent disk 30-1 and the second reagent disk 30-2. In addition, in the vicinity of the first reagent disk 30-1 and the second reagent disk 30-2, a first reagent dispensing mechanism 33-1 and a second reagent dispensing mechanism 33-2 are arranged, respectively. During reagent dispensing, using pipette nozzles, the first reagent dispensing mechanism 33-1 and the second reagent dispensing mechanism 33-2 aspirate reagents from the first reagent bottles 31-1 and the second reagent bottles 31-2 corresponding to test items at respective dispensing (aspiration) positions 30-1a and 30-2a on the first reagent disk 30-1 and the second reagent disk 30-2, and discharges the reagents into the corresponding reaction cells 11 at dispensing (discharge) positions 10b and 10c on the reaction disk 10. The reaction disk 10 is stored in the thermostat 12 and is held at a constant temperature of about 37° C.

Here, a photometer such as the absorptiometer 40 or the light scattering photometer 41 is arranged on the outer circumferential side of the reaction disk 10. Light emitted from light sources 42 and 43 arranged in the vicinity of the center portion on the inner circumferential side of the reaction disk 10 passes through the reaction cell 11 and is measured by the absorptiometer 40 or the light scattering photometer 41. This way, a measurement portion including the photometer and the light source that are arranged to face each other with the reaction disk 10 interposed therebetween configure the first measurement portion.

Photometry is executed on each of the reaction cells 11 accommodating a reaction solution as a mixed solution of a sample and a reagent whenever crossing the front of the absorptiometer 40 or the light scattering photometer 41 during the rotation operation of the reaction disk 10. An analog signal of absorbed light or scattered light measured by the photometer for each sample is input to an analog/digital (A/D) converter 62. The inside of the used reaction cell 11 is cleaned by a reaction cell cleaning mechanism 34 arranged in the vicinity of the reaction disk 10 such that the reaction cell 11 can be repeatedly used.

Next, a control system and a signal processing system in the automated analysis device 1 according to the present embodiment will be described. In this specification, the control system and the signal processing system will also be collectively referred to as "controller". The computer 60 is connected to the A/D converter 62 or a control computer 63 via an interface 61. The computer 60 instructs the control computer 63 to execute a control program that controls each of mechanism operations of the sample dispensing mechanism 22, the first reagent dispensing mechanism 33-1, the second reagent dispensing mechanism 33-2, and the like. In addition, the computer 60 is connected to a test information system 70 to configure an automatic analysis system.

In the drawing, the control computer 63 is connected to each of components and controls the entire automated analysis device. However, the respective components can also be configured to include controllers independently from each other.

A photometric value that is converted into a digital signal by the A/D converter 62 connected to the interface 61 is input to the computer 60. In addition, the memory 64 as the storage device is connected to the interface 61 and stores information such as reagent identification information, specimen identification information, an analysis parameter, an analysis item request content, a calibration result, or an analysis result based on the photometric value.

Next, among a biochemical test and a blood coagulation test of a sample using the photometer in the first measurement portion of the automated analysis device 1 of FIG. 1, an analysis operation of a first measurement item relating to a blood coagulation fibrinolytic marker such as D-dimer or FDP will be described. An analysis parameter relating to an item that is analyzable by the automated analysis device 1 is input by an operator in advance through an input portion such as a keyboard 66 or the operation screen 65 of the display portion of the computer 60, and is stored in the memory 64. In order to analyze a test item that is requested and instructed for each sample, the sample dispensing mechanism 22 dispenses a predetermined amount of sample from the specimen container 21 into the reaction cell 11 at the dispensing position 10a according to the analysis parameter.

The reaction cell 11 into which the sample is dispensed is transported by the rotation of the reaction disk 10 and stops at the dispensing (discharge) position 10b or 10c. The first reagent dispensing mechanism 33-1 and the second reagent dispensing mechanism 33-2 dispense a predetermined amount of reagent solution into the reaction cell 11 according to the analysis parameter of the corresponding test item. Regarding the dispensing order of the sample and the reagent, the reagent may be dispensed before the sample contrary to the example.

Whenever the reaction cell 11 crosses a photometric position, photometry is executed by the absorptiometer 40 or the light scattering photometer 41, and the analog value is converted by the A/D converter 62 into a numerical value as a signal value in proportion to the amount of absorbed light or scattered light. Next, the converted data is input to the computer 60 via the interface 61. In the configuration using the turntable reaction disk 10, specimens can be continuously dispensed by the rotation operation of the disk. Therefore, a high processing capacity can be obtained.

Next, in the computer 60, concentration data is calculated based on the numerical value data converted into the signal value as described above and calibration curve data that is measured in advance and stored using an analysis method designated for each test item, and is output to the operation screen 65.

The above-described concentration data can also be calculated in the control computer 63 instead of the computer 60.

Next, an analysis operation relating to the measurement of a hemostatic function test item, that is, the measurement of the blood coagulation time in the automated analysis device 1 according to the present embodiment will be described. A disposable reaction container 52 that is a reaction container accommodated in a reaction container accommodation portion 53 is transported to a sample dispensing station 54 by a reaction container transport mechanism 55. The sample dispensing mechanism 22 aspirates the sample from the specimen container 21 and dispenses the sample into the disposable reaction container 52 transported to the sample dispensing station 54 as described above.

Next, the disposable reaction container 52 into which the sample is dispensed is transported to the blood coagulation time measuring unit 50 configuring the second measurement portion by the reaction container transport mechanism 55 and is heated to 37° C. On the other hand, the reagent that is kept cool by the first reagent disk 30-1 is aspirated from the first reagent bottle 31-1 corresponding to the test item by the first reagent dispensing mechanism 33-1, is discharged into the empty reaction cell 11 loaded on the reaction disk 10, and is heated to about 37° C. Here, for example, the case where the reagent in the first reagent bottle 31-1 arranged in the first reagent disk 30-1 is used for analysis has been described. Depending on analysis conditions, the reagent in the second reagent bottle 31-2 arranged in the second reagent disk 30-2 can be also used for the measurement of the blood coagulation time.

After a given period of time is elapsed, the reagent accommodated in the reaction cell 11 that is heated as described above is aspirated by a reagent dispensing mechanism 56 having a reagent heating function, and is further heated (for example, 40° C.) in this mechanism. Here, as described above, the disposable reaction container 52 accommodating the sample that is heated to 37° C. as described above is transported to a measurement channel 51 in the blood coagulation time measuring unit 50 described below by the reaction container transport mechanism 55. Next, the reagent dispensing mechanism 56 having a reagent heating function discharges the heated reagent into the reaction container (disposable reaction container) 52. By discharging the reagent, a blood clotting reaction of the sample and the reagent in the reaction container 52 starts.

The blood coagulation time measuring unit 50 as the second measurement portion includes a plurality of measurement channels 51 each of which includes a light source and a light receiving unit. After the reagent is discharged as described above, the light receiving unit collects measurement data at predetermined short measurement time intervals (for example, 0.1 seconds). The collected measurement data is converted by the A/D converter 62 into a numerical value in proportion to the amount of light, and subsequently is input to the computer 60 via the interface 61.

The computer 60 acquires the blood coagulation time using the numerical value data converted as described above. Next, concentration data of a desired test item is acquired based on the acquired blood coagulation time and calibration curve data that is prepared and stored in advance depending on the test item, and is output to the operation screen 65 of the computer 60. In addition, the used disposable reaction container 52 is transported by the reaction container transport mechanism 55, and is disposed by a reaction container disposing portion 57. Here, the blood coagulation time and the concentration data can also be calculated by the control computer 63.

Here, in the blood coagulation time measuring unit 50, measurement data needs to be collected at the predetermined short measurement time intervals (for example, per 0.1 seconds) as described above. Therefore, only one reaction can be analyzed for one measurement channel 51.

In FIG. 1, for example, the blood coagulation time measuring unit 50 including six measurement channels 51 is illustrated. However, when all the measurement channels 51 are not empty, the automated analysis device 1 cannot receive the next measurement for the measurement item of the blood coagulation time and enters a standby state. Therefore, of course, the blood coagulation time measuring unit 50 can also be configured to include more than six measurement channels 51 depending on analysis conditions.

Next, identification of the specimen and reception of a measurement order in the automated analysis device according to the present embodiment will be described. FIG. 2 is a diagram illustrating an example of the specimen container loaded in the automated analysis device according to the present embodiment. As illustrated in the drawing, a specimen identifier 24 is attached to the specimen container 21 such that the specimen can be individually identified. As the specimen identifier 24, for example, a barcode or an RFID is used. Here, for example, a case where a barcode is used will be described. When the analysis starts, the sample disk 20 rotates clockwise or counterclockwise. Here, when each of the specimen containers 21 passes through the front of a sample barcode reading device 23 illustrated in FIG. 1, the sample barcode reading device 23 reads information of the barcode that is the specimen identifier 24 attached to the specimen container 21. The read information of the barcode is stored in the memory 64 of the computer 60 via the interface 61, and is managed as information for individually recognizing the specimen. Here, as the information of the barcode, an ID number of the specimen can be used. Alternatively, the information of the barcode may be information regarding at least one among a unique identifier, a blood collection date and time, an age, a gender, and a birth date for each patient.

In addition, the computer 60 of the automated analysis device 1 is connected to a test information system 70 to configure an automatic analysis system. First, in the test information system 70, when the barcode information is received from the computer 60 of the automated analysis device 1, the barcode information is compared to the specimen information that is stored in advance and managed in the test information system 70.

Here, the specimen information that is stored in advance and managed in the test information system 70 includes information such as urgent test information, a patient number, an order number, specimen test information, or specimen type information, which will be described below. These information can be preset from the user side, and can be stored and managed by inputting a correspondence between the specimen identification information and the urgent test information, the patient number, the order number, the specimen test information, the specimen type information, and the like.

When the information managed in the test information system 70 matches the barcode information received by the computer 60 as a result of the comparison, some or all of the urgent test information, the patient number, the order number, the specimen test information, the specimen type information, and the like belonging to the managed specimen information are transmitted to the computer 60. On the other hand, when the information managed in the test information system 70 does not match the barcode information received by the computer 60, error of communication abnormality is output.

FIG. 3 illustrates the information such as the specimen identification information or the specimen information that is handled by the automated analysis device according to the present embodiment. In the automated analysis device 300, specimen information 301 is stored for each specimen. As illustrated in the drawing, the specimen information 301 includes: urgent test information 302 representing whether or not to be an urgent test target; a patient number 303 for identifying the same patient; an order number 304 for distinguishing between test request timings, for example, when a test is executed multiple times for one day for the same patient; loading position information 305 representing a loading position of the specimen on the automated analysis device; specimen test information 306 representing a measurement item and a measurement result; and specimen type information 307 representing the type of the specimen.

Further, the specimen information 301 includes: loading order information 308 representing an order in which the automated analysis device 300 recognizes the specimen; a measurement completion time 309 representing a measurement completion time or a measurement completion estimated time of the specimen; measurement completion information 310 representing whether the measurement is started or completed; an earliest measurement completion time for other specimens 311 representing an earliest measurement completion time or measurement completion estimated time for other specimens of the same patient; and measurement waiting order information 312 representing a measurement order for specimens on which measurement is not started. The specimen information 301 is stored in the computer 60 or the like.

The urgent test information 302, the patient number 303, the order number 304, the loading position information 305, the specimen test information 306, and the specimen type information 307 in the specimen information 301 are acquired from a screen, an external system, or an external medium based on the specimen identification information 313 attached to the blood collection tube.

FIG. 4 schematically illustrates a timing at which information is input to the specimen information 301 for each specimen. The urgent test information 302, the patient number 303, the order number 304, the loading position information 305, the specimen test information 306, and the specimen type information 307 are input from a screen, an external system, or an external medium based on the specimen identification 313 for each specimen. The input timing may be the time when the automated analysis device recognizes the specimen or before the automated analysis device recognizes the specimen. When the automated analysis device recognizes the specimen, the loading order information 308 is input.

When the measurement of each specimen is started, the measurement start is input to the measurement completion information 310, and the measurement completion estimated time is input to the measurement completion time 309. In addition, the loading order information 308 and the measurement waiting order information 312 are cleared. When the measurement of each specimen is completed, complete information is input to the measurement completion information 310, the measurement completion time is input to the measurement completion time 309, and the measurement result is input to the specimen test information 306.

When the automated analysis device recognizes the specimen, the measurement order is determined. The measurement waiting order information 312 in the specimen information 301 is set as the measurement order. A method of determining the measurement order will be described. When the next measurement completion time 309 is compared to the earliest measurement completion time for other specimens 311, in a case where the measurement completion time 309 and the earliest measurement completion time for other specimens 311 are not input, the measurement completion time is handled as the latest time.

First, using the patient number 303 and the order number 304 as key information, the earliest measurement completion time 309 for other specimens of the same patient is input to the earliest measurement completion time for other specimens 311. When a target that is another specimen of the same patient is not present, the earliest measurement completion time 309 for other specimens of the same patient is not input.

FIG. 5 illustrates an example of input flows of the earliest measurement completion time for other specimens 311. When all the specimen information (501) as a target are compared to each other for the patient number 303 (502) or for the order number 304 (503), a plurality of the specimen information having the same patient number 303 or the same order number 304 are set as other specimens for the same patient. When the measurement completion time 309 of the specimen information 301 for other specimens of the same patient is compared to the earliest measurement completion time for other specimens 311 of the specimen information 301 of the currently recognized specimen (504), the earlier time is input to the earliest measurement completion time for other specimens 311 of the specimen information 301 of the currently recognized specimen (505).

That is, when the computer 60 recognizes a new specimen, the computer 60 compares the new specimen to other specimens for the same patient and the same order for the earliest measurement completion time for other specimens 311 based on the specimen information 301, and executes a control such that an earlier time is input to the earliest measurement completion time for other specimens 311 of the specimen information 301 of the new specimen.

Next, the specimen information 301 of a target for which the measurement waiting order information 312 is to be reset is extracted. FIG. 6 is an example of flows for extracting a measurement waiting order information resetting target specimen. Whether or not the input of the loading order information 308 is completed is checked for all the specimen information (601) as a target (602), and when the input of the loading order information 308 is completed, whether or not the measurement completion information 310 is input is checked (603). The specimen information 301 for which the loading order information 308 is input and the measurement completion information 310 is not input is set as a target for which the measurement waiting order information 312 is to be reset (604). After checking all the specimen information, the measurement waiting order information 312 of the measurement waiting order information resetting target specimens including the currently recognized specimen are reset. That is, the computer 60 executes a control to set, as a target for which the measurement waiting order information is to be reset, all the stored specimen information for which the loading order information is input and the specimen information for which the measurement completion information is not input and the specimen information of the new specimen.

Further, process flows set when the urgent test information 302 of the currently recognized specimen is urgent are not different those set when the urgent test information 302 of the currently recognized specimen is not urgent. When the urgent test information 302 of the currently recognized specimen is urgent, the reset is executed according to measurement waiting order information resetting process flows illustrated in FIG. 7. When the urgent test information 302 of the currently recognized specimen is not urgent, the reset is executed according to measurement waiting order information resetting process flows illustrated in FIG. 8.

In FIG. 7, whether or not the measurement waiting order information resetting target specimen is present is checked (701). When the measurement waiting order information resetting target specimen is not present, the measurement waiting order information 312 of the currently recognized urgent specimen is set as 1 (702), and the process ends. When the measurement waiting order information resetting target specimen is present, the urgent currently recognized specimen is compared to the target specimen for which the measurement waiting order information 312 is 1 (703). The currently recognized specimen is compared to the measurement waiting order information resetting target specimen for which the urgent test information 302 is urgent (704). The earliest measurement completion time for other specimens 311 of the currently recognized specimen is compared to the earliest measurement completion time for other specimens 311 of the specimen to be compared (705). When the earliest measurement completion time for other specimens 311 of the currently recognized specimen is earlier, the measurement waiting order information 312 of the currently recognized specimen is set as the measurement waiting order information 312 of the specimen to be compared (706), and 1 is added to the measurement waiting order information 312 of specimens after the specimen to be compared. 1 is also added to the measurement waiting order information 312 of the measurement waiting order information resetting target specimen for which the urgent test information 302 is not urgent, and the process ends (707).

The earliest measurement completion time for other specimens 311 of the currently recognized specimen is compared to the earliest measurement completion time for other specimens 311 of the specimen to be compared (705). When the earliest measurement completion time for other specimens 311 of the currently recognized specimen is later, the currently recognized specimen is compared to the measurement waiting order information resetting target specimen for which the measurement waiting order information 312 is the next (708). After the comparison to all the measurement waiting order information resetting target specimens for which the urgent test information 302 is urgent is completed, the measurement waiting order information 312 of the currently recognized specimen is set as the final order among the measurement waiting order information resetting target specimens for which the urgent test information 302 is urgent (709). Next, 1 is added to the measurement waiting order information 312 of the measurement waiting order information resetting target specimens for which the urgent test information 302 is not urgent (710).

This way, when the urgent test information of the new specimen is urgent, the computer 60 checks whether or not a target for which the measurement waiting order information is to be reset is present. When the target for which the measurement waiting order information is to be reset is not present, the computer 60 sets the measurement waiting order information 312 of the specimen information 301 of the new specimen as 1. When the target for which the measurement waiting order information is to be reset is present, the computer 60 compares the measurement waiting order information resetting target specimen for which the urgent test information is urgent to the new specimen for the earliest measurement completion time for other specimens. When the earliest measurement completion time for other specimens of the new specimen is earlier, the computer 60 executes a control to set the measurement waiting order information of the new specimen as the measurement waiting order information of the specimen to be compared.

When the urgent test information 302 of the currently recognized specimen is not urgent, according to the process flows illustrated in FIG. 8, the computer 60 compares the currently recognized specimen to the measurement waiting order information resetting target specimens for which the urgent test information 302 is not urgent in order from a target specimen for which the measurement waiting order information 312 is the lowest (801). The currently recognized specimen is compared to the measurement waiting order information resetting target specimen for which the urgent test information 302 is not urgent (802). The earliest measurement completion time for other specimens 311 of the currently recognized specimen is compared to the earliest measurement completion time for other specimens 311 of the specimen to be compared (803). When the earliest measurement completion time for other specimens 311 of the currently recognized specimen is earlier, the measurement waiting order information 312 of the currently recognized specimen is set as the measurement waiting order information 312 of the specimen to be compared (804), 1 is added to the measurement waiting order information 312 of specimens after the specimen to be compared, and the process ends (805).

When the urgent test information 302 of the new specimen is not urgent, the computer 60 compares the currently recognized specimen to the measurement waiting order information resetting target specimens for which the urgent test information 302 is not urgent for the earliest measurement completion time for other specimens 311 in order from a target specimen for which the measurement waiting order information 312 is the lowest. When the earliest measurement completion time for other specimens of the new specimen is earlier, the computer 60 sets the measurement waiting order information of the new specimen as the measurement waiting order information of the specimen to be compared.

In addition, the earliest measurement completion time for other specimens 311 of the currently recognized specimen is compared to the earliest measurement completion time for other specimens 311 of the specimen to be compared (803). When the earliest measurement completion time for other specimens 311 of the currently recognized specimen is later, the currently recognized specimen is compared to the measurement waiting order information resetting target specimen for which the measurement waiting order information 312 is the next (806). When the comparison to all the measurement waiting order information resetting target specimens for which the urgent test information 302 is not urgent is completed, the measurement waiting order information 312 of the currently recognized specimen is set as the final order (807).

FIG. 9 illustrates a measurement order monitor screen 900 as an example of a screen that monitors the measurement waiting order for specimens in the computer 60 of the automated analysis device according to the present embodiment. That is, the computer 60 as the controller executes a control such that the measurement waiting order for specimens is displayed on the operation screen 65. Further, when a title portion 901 of the measurement order monitor screen 900 is clicked, information is sorted and displayed by using information of the clicked column such as the patient number as key information. Further, when a same patient specimen monitor button 903 of the drawing is clicked, the screen is changed to a screen illustrated in FIG. 10, for example, for a specimen having a measurement order of 3 that is selected in a data portion 902.

FIG. 10 illustrates an example in which the computer 60 displays a same patient specimen monitor screen 1000 on the operation screen 65 as a screen example that monitors measurement statuses of specimens for the same patient and the same order based on the patient number (000101) and the order number (003) of the measurement order 3. That is, the computer executes a control such that measurement statuses of specimens for the same patient and the same order are displayed on the operation screen 65. That is, when a measurement result button 1002 is clicked, the measurement results of the specimens for the same patient and the same order can be collectively output. As a result, when the same type of test needs to be measured multiple times for specimens for the same patients at a predetermined time interval, the computer as the controller can organize and output the measurement results using the stored specimen information such as the patient number or the measurement completion time. Therefore, a load on the user can be reduced. Further, when a sample disk position monitor screen button 1001 is clicked, the screen is changed to a sample disk position monitor screen.

FIG. 11 illustrates a sample disk position monitor screen 1100 based on the patient number (000101) and the order number (003) as an example of a screen that monitors positions of specimens for the same patient and the same order on the sample disk in the computer 60 of the automated analysis device according to the present embodiment. Display positions of three black circles in the drawing represent the positions of the specimens. That is, the computer 60 executes a control such that the positions of the specimens on the specimen container holder portion are displayed on the operation screen 65.

FIG. 12 illustrates a same patient specimen setting screen example on the operation screen of the computer 60 of the automated analysis device according to the present embodiment. That is, a same patient specimen setting screen 1200 is displayed on which a specimen type and a test item as a target are set when other specimens for the same patient are searched in a case where a measurement waiting order is determined. In other words, the computer 60 controls the operation screen 65 to display a screen on which a specimen type and a test item of a target specimen can be set when other specimens for the same patient are searched in a case where a measurement order for specimens waiting to be measured is determined.

The same patient specimen setting screen 1200 of the drawing displays a state where serum is set as the specimen type. Setting information of the specimen type selected in a tab portion 1202 displaying the specimen type name is displayed on a specimen type enabling/disabling setting portion 1201. That is, enabling and disabling can be switched by clicking the specimen type enabling/disabling setting portion 1201.

A target test item of the specimen type selected in the tab portion 1202 displaying the specimen type name displays a test item list 1203. Setting information of each item is displayed on a test item enabling/disabling setting portion 1204. That is, the user can switch between enabling and disabling by clicking the test item enabling/disabling setting portion 1204.

In the automated analysis device according to the present embodiment described above in detail, when a measurement order for a newly recognized specimen is determined, a measurement order for specimens waiting to be measured is changed with reference to measurement completion times or urgent test information of other specimens for the same patient having the same patient number such that a time difference between specimen measurement result output timings for a plurality of specimens for the same patient can be minimized. In addition, even in a situation where the measurement start time itself largely varies depending on a difference in the time required for a pre-treatment, delayed reporting to clinical sites can be minimized.

Further, when the same type of test needs to be executed multiple times for specimens for the same patient at predetermined time intervals, for example, when a glycemic load test as a test required for diagnosis of diabetes is executed, the computer as the controller can organize and output the measurement results using the stored specimen information such as the patient number or the measurement completion time. Therefore, a load on the user can be reduced.

The present invention is not limited to the embodiment described above and includes various modification examples. For example, the embodiments have been described in detail for easy understanding of the present invention, and the present invention is not necessarily to include all the configurations described above.

Further, the example in which some or all of the above-described respective configurations, functions, computers, and the like are implemented by creating programs has been mainly described. However, some or all of the above-described respective configurations, functions, computers, and the like may be implemented by hardware, for example, by designing an integrated circuit. That is, some or all of the functions of the processing units may be implemented with an integrated circuit such as an Application Specific Integrated Circuit (ASIC) or a Field Programmable Gate Array (FPGA).

REFERENCE SIGNS LIST

1, 300: automated analysis device
10: reaction disk
11: reaction cell
12: thermostat
20: sample disk
21: specimen container
22: sample dispensing mechanism
23: sample barcode reading device
24, 313: specimen identifier
30: reagent disk
31: reagent bottle
32: reagent barcode reading device
33: reagent dispensing mechanism
34: reaction cell cleaning mechanism
40: absorptiometer
41: light scattering photometer
42, 43: light source
50: blood coagulation time measuring unit
51: measurement channel
52: disposable reaction container
53: reaction container accommodation portion
54: sample dispensing station
55: reaction container transport mechanism
56: reagent dispensing mechanism having a reagent heating function
57: reaction container disposing portion
60: computer
61: interface
62: A/D converter
63: control computer
64: memory
65: operation screen
66: keyboard
70: test information system
301: specimen information
302: urgent test information
303: patient number
304: order number
305: loading position information
306: specimen test information
307: specimen type information
308: loading order information
309: measurement completion time
310: measurement completion information
311: earliest measurement completion time for other specimens
312: measurement waiting order information
900: measurement order monitor screen
901: title portion
902: data portion
903: same patient specimen monitor button 1000: same patient specimen monitor screen
1001: sample disk position monitor screen button
1002: measurement result button
1100: sample disk position monitor screen
1200: same patient specimen setting screen
1201: specimen type enabling/disabling setting portion
1202: tab portion
1203: test item list
1204: test item enabling/disabling setting portion

The invention claimed is:

1. An automated analysis device that tests a plurality of test fields, the device comprising:
a specimen container holder portion that holds a specimen container accommodating a specimen;
a reagent container holder portion that holds a reagent container accommodating a reagent;
a dispensing mechanism that dispenses the specimen and the reagent;
a reaction cell holder portion that holds a plurality of reaction cells accommodating a mixed solution of the specimen and the reagent;
a first measurement portion that detects light with which the mixed solution is irradiated;
a second measurement portion that includes a plurality of measurement channels each of which holds a reaction container accommodating the mixed solution and that detects light with which the reaction container held by each of the measurement channels is irradiated; and
a controller that controls a test of the specimen based on specimen identification information read from the specimen container,
wherein the controller is configured to:
store specimen information including a patient number read from the specimen identification information, a measurement completion time of the test of the specimen, an order number, and an earliest measurement completion time for other specimens,
determine a measurement order for specimens waiting to be measured based on the stored patient number and the stored measurement completion time, and
control the automated analysis device to perform the plurality of test fields on the specimen based on the specimen information and the measurement order; and
wherein the controller is configured to recognize a new specimen and compare the new specimen to another specimen for the same patient and the same order for the earliest measurement completion time for other specimens of the specimen information based on the specimen information, and execute a control such that an earlier time is input to the earliest measurement completion time for other specimens of the specimen information of the new specimen.

2. The automated analysis device according to claim 1, wherein the plurality of test fields include a biochemical test, an immunological test, and a blood coagulation test.

3. The automated analysis device according to claim 1, wherein the specimen information further includes loading order information, measurement completion information, and measurement waiting order information, and
the controller is configured to set, as a target for which the measurement waiting order information is to be reset, all the stored specimen information for which the loading order information is input and the specimen information of the measurement completion information is not input and the specimen information of the new specimen.

4. The automated analysis device according to claim 3, wherein the specimen information includes urgent test information,
when the urgent test information of the new specimen is urgent, the controller is configured to check whether or not a target for which the measurement waiting order information is to be reset is present,
when the target for which the measurement waiting order information is to be reset is not present, the controller is configured to set the measurement waiting order information of the specimen information of the new specimen as 1,
when the target for which the measurement waiting order information is to be reset is present, the controller is configured to compare the measurement waiting order resetting target specimen for which the urgent test information is urgent to the new specimen for the earliest measurement completion time for other specimens, and
when the earliest measurement completion time for other specimens of the new specimen is earlier, the controller is configured to set the measurement waiting order information of the new specimen as the measurement waiting order information of the specimen to be compared.

5. The automated analysis device according to claim 4, wherein when the urgent test information of the new specimen is not urgent, the controller is configured to compare the new specimen to the measurement waiting order information resetting target specimens for which the urgent test information is not urgent for the earliest measurement completion time for other specimens in order from a target specimen for which the measurement waiting order information is the lowest, and
when the earliest measurement completion time for other specimens of the new specimen is earlier, the controller is configured to set the measurement waiting order information of the new specimen as the measurement waiting order information of the specimen to be compared.

6. The automated analysis device according to claim 1, wherein the controller includes a display portion that displays a measurement waiting order of the specimen.

7. The automated analysis device according to claim 6, wherein the controller is configured to control the display portion to display measurement statuses of specimens for the same patient and the same order and positions of the specimens on the specimen container holder portion.

8. The automated analysis device according to claim 6, wherein the controller is configured to control the display portion to display a screen on which a specimen type and a test item of a target specimen can be set when other specimens for the same patient are searched in a case where a measurement order for specimens waiting to be measured is determined.

* * * * *